US011255811B2

(12) United States Patent
Liu et al.

(10) Patent No.: US 11,255,811 B2
(45) Date of Patent: Feb. 22, 2022

(54) SENSOR FOR LEAD DETECTION (71) Applicant: CASE WESTERN RESERVE UNIVERSITY, Cleveland, OH (US)

(72) Inventors: Chung Chiun Liu, Cleveland, OH (US); Yifan Dai, Cleveland, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 181 days.

(21) Appl. No.: 16/608,527

(22) PCT Filed: Apr. 25, 2018

(86) PCT No.: PCT/US2018/029450
§ 371 (c)(1),
(2) Date: Oct. 25, 2019

(87) PCT Pub. No.: WO2018/200731
PCT Pub. Date: Nov. 1, 2018

(65) Prior Publication Data
US 2020/0182821 A1 Jun. 11, 2020

Related U.S. Application Data (60) Provisional application No. 62/489,722, filed on Apr. 25, 2017.

(51) Int. Cl.
G01N 27/333 (2006.01)
G01N 27/411 (2006.01)
(Continued)

(52) U.S. Cl.
CPC ......... *G01N 27/333* (2013.01); *G01N 27/411* (2013.01); *G01N 27/42* (2013.01); *G01N 33/182* (2013.01)

(58) Field of Classification Search
CPC ...... G01N 27/48; G01N 27/49; G01N 27/333; G01N 33/1813
See application file for complete search history.

(56) References Cited

U.S. PATENT DOCUMENTS 5,518,956 A 5/1996 Liu et al.
5,785,830 A 7/1998 Foos et al.
(Continued)

FOREIGN PATENT DOCUMENTS

WO 2017027477 A1 2/2017

OTHER PUBLICATIONS

Zou et al.. "Environmentally friendly disposable sensors with microfabricated on-chip planar bismuth electrodes in situ heavy metal ions measurements," Sensors and Actuators B: Chemical 134 (2008) 18-24 (Year: 2008).*

(Continued)

*Primary Examiner* — Alexander S Noguerola
(74) *Attorney, Agent, or Firm* — Tarolli, Sundheim, Covell & Tummino LLP (57) ABSTRACT A sensor for the detection of lead includes a substrate, a working electrode formed on a surface of the substrate, a counter electrode formed on the surface of the substrate, a dielectric layer covering a portion of the working electrode and counter electrode and defining an aperture exposing other portions of the working electrode and counter electrode. The working electrode includes a metalized film with working surface and a monolayer (or bilayer) of bismuth deposited on the working surface by underpotential deposition.

14 Claims, 7 Drawing Sheets (51) Int. Cl.
*G01N 27/42* (2006.01)
*G01N 33/18* (2006.01)

(56) References Cited

U.S. PATENT DOCUMENTS

| | | |
|---|---|---|
| 2008/0027135 A1 | 1/2008 | Sondek et al. |
| 2012/0046181 A1 | 2/2012 | Harb et al. |
| 2017/0089861 A1 | 3/2017 | Chen et al. |

OTHER PUBLICATIONS

Cadle et al., "Ring-disk Electrode Study of the Reduction and Oxidation of Bismuth on Gold," J. Electrochem. Soc.: Electrochemical Science and Technology Sep. 1977, pp. 1166-1169 (Year: 1977).*

Hara et al., "In situ STM study of underpotential deposition of bismuth on Au(110) in perchloric acid solution," Electrochimica Acta 51 (2006) 2327-2332 (Year: 2006).*

Zhu et al., "On-chip generated mercury microelectrode for heavy metal ion detection," Lab Chip, 2005, 5, 212-217 (Year: 2005).*

Q. Xue, et al. "An integrated micro immunosensor for hemoglobin-A1c level detection", In Pr5oceedings of 2010 IEEE/ASME International Conference on Mechatronic and Embedded Systems and Applications, p. 208-212, (Year: Jul. 2010).

First Named Inventor: Chung Chiun Liu; Title: System and Methods for the Detection of Biomarkers of Neurodegenerative Disorders; U.S. Appl. No. 15/970,738, filed May 3, 2018; Final Office Action; Notification Date: Sep. 22, 2020.

First Named Inventor: Chung Chiun Liu; Title: System and Methods for the Detection of HBA1C; U.S. Appl. No. 15/973,218, filed May 7, 2018; Final Office Action; Notification Date: Sep. 1, 2020.

First Named Inventor: Chung Chiun Liu; Title: System and Method for Detecting Lysyl Oxidase-Like 2 Protein (LOXL2) and Breast Cancer; U.S. Appl. No. 16/168,630, filed Oct. 23, 2018; Office Action; Notification Date: Sep. 21, 2020; 7 pgs.

First Named Inventor: Chung Chiun Liu; Title: System and Methods for the Detection of Biomarkers of Glypican-1; U.S. Appl. No. 16/118,216, filed Aug. 30, 2018; Final Office Action; Notification Date: Oct. 8, 2020.

Karalemas et al., Talanta, 2000, 53:391-402.

Moreno-Bueno, et al., EMBO Mol Med., 2011, 3:528-544.

* cited by examiner

SENSOR FOR LEAD DETECTION

RELATED APPLICATION

This application claims priority from U.S. Provisional Application No. 62/489,722, filed Apr. 25, 2017, the subject matter of which is incorporated herein by reference in its entirety.

BACKGROUND

Lead is a highly poisonous metal both to the human body and the environment. Children lead poisoning is considered a major environmental health problem. The central nervous system can be severely damaged from lead toxicity. Lead level as low as 10 µg/dl in human blood can threaten children's ability in learning and behavior. A high lead level (>70 µg/dL) can cause catastrophic health problems, including coma, seizures and even death. The main exposure of lead to human is through water sources. The lead levels in environmental and biological samples should be quantitial to protect children from lead contamination.

Water sources polluted with lead can devastating to human health. Currently, lead still exists in metal water taps and interior water pipes. Corrosion of older fixtures and solders from water pipes results in lead leaching into drinking water. Lead is neither visible nor can be smelled or tasted by humans. The only method to detect whether lead is in water is to test a water sample from the tap water or water sources, which can take a couple of days to. Consequently, a simpler and more efficient measurement technology for lead ions in water will be of practical and scientific importance.

Widely applied analytical methods for lead determination, including flame atomic absorption spectrometry (FAAS), electro-thermal atomic adsorption spectrometry (ET-AAS), inductively coupled plasma mass spectrometry (ICP-MS), and inductively coupled plasma optical emission spectrometry (ICP-OES), are all characterized by high costs and intricate instrumentation.

SUMMARY

Embodiments described herein relate to a sensor for detecting, identifying, quantifying, and/or determining the amount or level of lead in a sample, and particularly relates to a sensor for detecting, identifying, quantifying, and/or determining the amount or level of lead in a sample, such as water or other fluids.

The sensor includes a substrate, a working electrode formed on a surface of the substrate, a counter electrode formed on the surface of the substrate, a dielectric layer covering a portion of the working electrode and counter electrode and defining an aperture exposing other portions of the working electrode and counter electrode.

The working electrode includes a metalized film with a working surface and a monolayer (or bilayer) of bismuth deposited on the surface by underpotential deposition. The surface of the metalized film is substantially free of surface adsorbed impurities between the metalized film and the monolayer.

In some embodiments, metalized films used to form the working electrode and the counter electrode can independently comprise gold, platinum, palladium, silver, carbon, alloys thereof, and composites thereof. The metalized films can be provided on the surface of the substrate by sputtering or coating the films on the surface and then laser ablating the films to form the working electrode and counter electrode.

In other embodiments, the sensor can include a reference electrode on the surface of the substrate. The dielectric can cover a portion of the reference electrode. The sensor can also include a measuring device for applying voltage potentials to the working electrode and counter electrode and measuring the current flow between the working electrode and counter electrode to determine the level of the lead in a sample, such as a drinking water.

Other embodiments described herein relate to a method of detecting the quantity of lead in an aqueous sample, such as drinking water. The method includes providing a sensor that includes a substrate, a working electrode formed on a surface of the substrate, a counter electrode formed on the surface of the substrate, a dielectric layer covering a portion of the working electrode and a counter electrode and defining an aperture exposing other portions of the working electrode and counter electrode. The working electrode includes a metalized film with working surface and a monolayer or bilayer of bismuth deposited on the working surface by underpotential deposition.

A volume of an aqueous sample is applied on the working electrode for a duration of time effective to allow lead ions in the sample to complex with the deposited bismuth. The complexed lead ions are anodically stripped from the working electrode and an anodic stripping current is measured during anodic stripping. The measured anodic stripping current is then compared to a control value to detect the quantity of lead ions in the aqueous sample. In some embodiments, the complexed lead ions are anodically stripped by differential pulse voltametry. In other embodiments, the control value is a calibration curve.

DETAILED DESCRIPTION

Unless specifically addressed herein, all terms used have the same meaning as would be understood by those of skilled in the art of the subject matter of the application. The following definitions will provide clarity with respect to the terms used in the specification and claims.

As used herein, the term "quantitative data" or "quantitative level" or "quantitative amount" refers to data, levels, or amounts associated with any dataset components (e.g., markers, clinical indicia) that can be assigned a numerical value.

As used herein, the terms "control" or "control sample" refer to one or more samples in which the concentration of the lead is known.

Embodiments described herein relate to a sensor for detecting, identifying, quantifying, and/or determining the amount or level of lead in a sample, and particularly relates to a disposable, and cost-effective sensor for detecting, identifying, quantifying, and/or determining the amount or level of lead in a sample, such as tap or drinking water.

The sensor includes a substrate, a working electrode formed on a surface of the substrate, a counter electrode formed on the surface of the substrate, a dielectric layer covering a portion of the working electrode and counter electrode and defining an aperture exposing other portions of the working electrode and counter electrode.

The working electrode includes a metalized film with a working surface and a monolayer (or bilayer) of bismuth deposited on the surface by underpotential deposition. The underpotential deposition provides the deposition on an atomic monolayer or few monolayers and this will enhance the sensitivity of the detection, in this case, the lead ions in the water environment. Underpotential deposition is a process in which a reduction of a metal cation to a solid metal (substrate) occurs. The potential that applies to the deposited metal is slightly lower than the reduction potential of the metal. The applied potential for deposition of bismuth onto the surface of a metalized film (e.g., gold film) is slightly lower than the standard reduction potential of bismuth per se.

The metalized films used to form the working electrode and the counter electrode can independently comprise gold, platinum, palladium, silver, carbon, alloys thereof, and composites thereof. The metalized films can be provided on the surface of the substrate by sputtering or coating the films on the surface and then laser ablating the films to form the working electrode and counter electrode.

Figure 1:
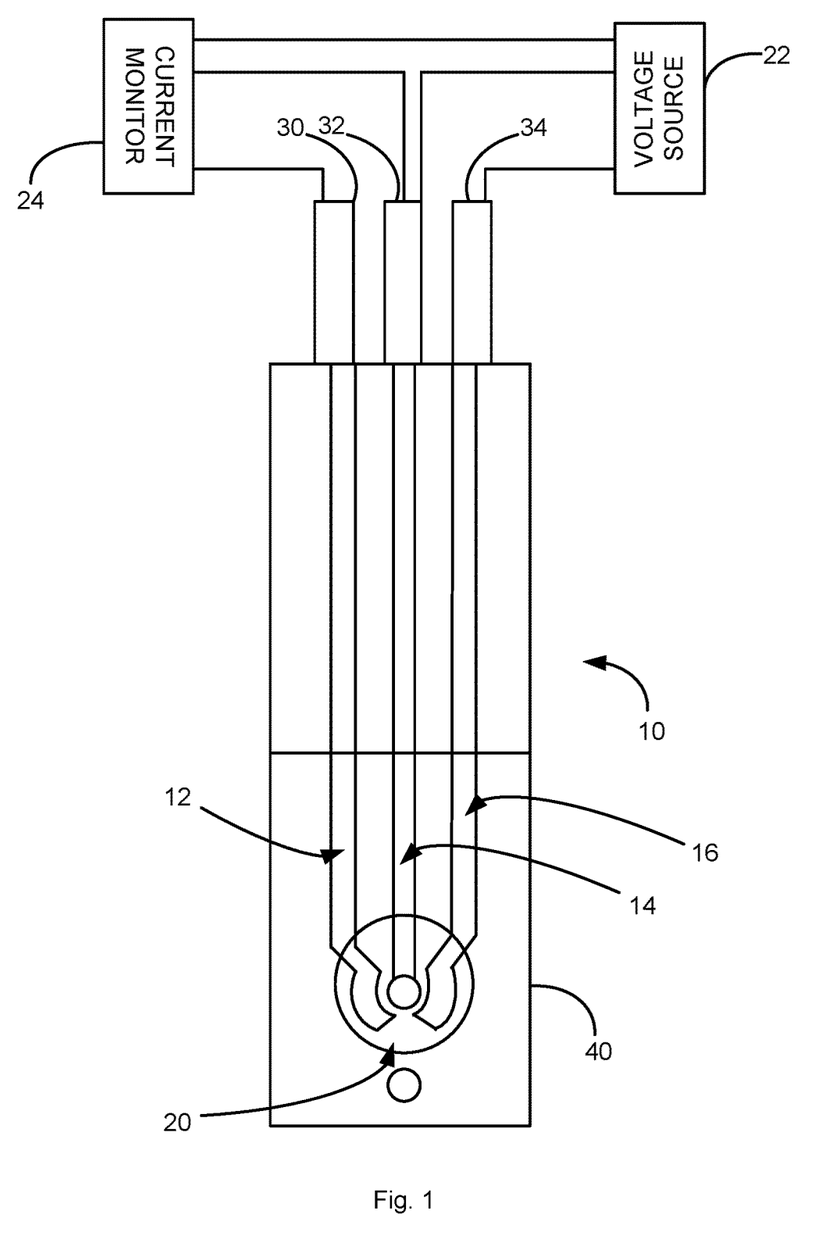
FIG. 1 is a schematic illustration of a sensor in accordance with an aspect of the application.

FIG. 1 illustrates a sensor 10 in accordance with an embodiment of the application. The sensor 10 is a three-electrode sensor including a counter electrode 12, a working electrode 14, and a reference electrode 16 that are formed on the surface of a substrate. A dielectric layer 40 covers a portion of the working electrode 12, counter electrode 14 and reference electrode 16. The dielectric layer 40 includes an aperture 20 which define a detection region of the working electrode 12, counter electrode 14, reference electrode 16 that is exposed to samples in which the level of lead is detected.

The working electrode 14 include a metalized film with working surface and a monolayer (or bilayer) of bismuth deposited on the surface by underpotential deposition. The surface of the metalized film is substantially free of surface adsorbed impurities between the metalized film and the monolayer.

A voltage source 22 is connected to the working and reference electrodes 14, 16. A current measuring device 24 is connected to the working and counter electrodes 14, 12 to measure the current when a sample containing lead contacts the detection region 20 of the sensor 10.

The lead sensor can be made using a thin film, thick film, and/or ink-jet printing technique, especially for the deposition of multiple electrodes on a substrate. The thin film process can include physical or chemical vapor deposition. Electrochemical sensors and thick film techniques for their fabrication are discussed in U.S. Pat. No. 4,571,292 to C. C. Liu et al., U.S. Pat. No. 4,655,880 to C. C. Liu, and co-pending application U.S. Ser. No. 09/466,865, which are incorporated by reference in their entirety.

In some embodiments, the working electrode, counter electrode, and reference electrode may be formed using laser ablation, a process which can produce elements with features that are less than one-thousandth of an inch. Laser ablation enables the precise definition of the working electrode, counter electrode, and reference electrode as well as electrical connecting leads and other features, which is required to reduce coefficient of variation and provide accurate measurements. Metalized films, such as Au, Pd, and Pt or any metal having similar electrochemical properties, that can be sputtered or coated on plastic substrates, such as PET or polycarbonate, or other dielectric material, can be irradiated using laser ablation to provide these features.

In one example, a gold film with a thickness of about 300 to about 2000 A can be deposited by a sputtering technique resulting in very uniform layer that can be laser ablated to form the working and counter electrodes. The counter electrode can use other materials. However, for the simplicity of fabrication, using identical material for both working and counter electrodes will simplify the fabrication process providing the feasibility of producing both electrodes in a single processing step. An Ag/AgCl reference electrode, the insulation layer, and the electrical connecting parts can then be printed using thick-film screen printing technique.

In some embodiments, the overall dimensions of an individual sensors are chosen to be $33.0 \times 8.0$ mm$^2$. The total width of each individual biosensor is approximately 2.8 mm with a working electrode of 1.0 mm in diameter sufficiently to accommodate up to a 5 µL sample volume. These sizes can be changed as needed.

In some embodiments, a three-electrode base electrochemical sensor can be formed where both working and counter electrodes are thin gold films of about 10 nm in thickness. Other metals can also be used for the fabrication of the working and the counter electrodes. The thin gold film can be deposited using roll-to-roll sputtering technique. Hence, the production of the gold-film based sensor is very cost effective and the gold electrode elements are very uniform and reproducible which are very practical and unique for single-use, in situ applications. Any other similar technique in deposition of any other metals can be used.

The reference electrode can be a thick-film printed Ag/AgCl electrode. Other types of the reference electrode and the formation method of the reference electrode can also be employed. In one example, the overall dimensions of an individual sensor were $33.0 \times 8.0$ mm$^2$. The working electrode area was 1.54 mm$^2$ accommodating 10-15 µL of liquid test sample. The dimensions and configuration of this sensor can be varied. The employment of known micro-fabrication processes, such as sputtering physical vapor deposition, laser ablation and thick film printing techniques resulting in producing a high-reproducible and low-cost single-use disposable biosensors.

A 3-step pretreatment procedure can be applied to the sensor in order to eliminate any naturally formed oxide of the gold or other metal surface resulting in a significant increase in the electrode charge transfer ability and enhancement in the reproducibility of the sensor. Typically, a batch of 8 sensors can be immersed in a 2M KOH solution for 15 min. Any other number of the sensors used in a batch is an option and also covered by this disclosure. After rinsing with copious amount of deionized (DI) water, the sensors are placed in 0.05 M concentrated $H_2SO_4$ solution (95.0 to 98.0 w/w %) for another 15 min. DI water is then used to rinse the sensor prototypes. The sensors are then placed in a 0.05 M concentrated $HNO_3$ solution (70% w/w %) for another 15 minutes. The sensors are rinsed once more time with DI water and are dried in a steam of nitrogen. Other concentration of the KOH, $H_2SO_4$ and $HNO_3$ can also be used. The selected concentrations of the chemicals used in this chemical pretreatment step is to maintain the integrity of the thin gold film based sensor and retaining the clean surface of the electrode elements. Other means to accomplish this objective is also covered by this disclosure, including using ethanol and DI water cleaning procedure.

Underpotential deposition is applied for the formation of the bismuth monolayer or bilayer on the surface of working electrode. Cyclic voltammetry can be applied for bismuth deposition. By way of example, 0.1M of Bismuth (III) nitrate pentahydrate was mixed in 1M of nitric acid with 1 Mm of sodium chloride based on aqueous solution. Fixed potential sweep from −0.45V to −0.35V of cyclic voltammetry was used for the under-potential deposition of bismuth on a gold electrode. After deposition, the bismuth sensor can be rinsed by deionized water and dried by nitrogen air gently. Prepared sensors can be stored in the refrigerator at 4° C. and ready for detection of lead ions. The applied electro-potential range can be varied and is covered by this disclosure.

Figure 2:
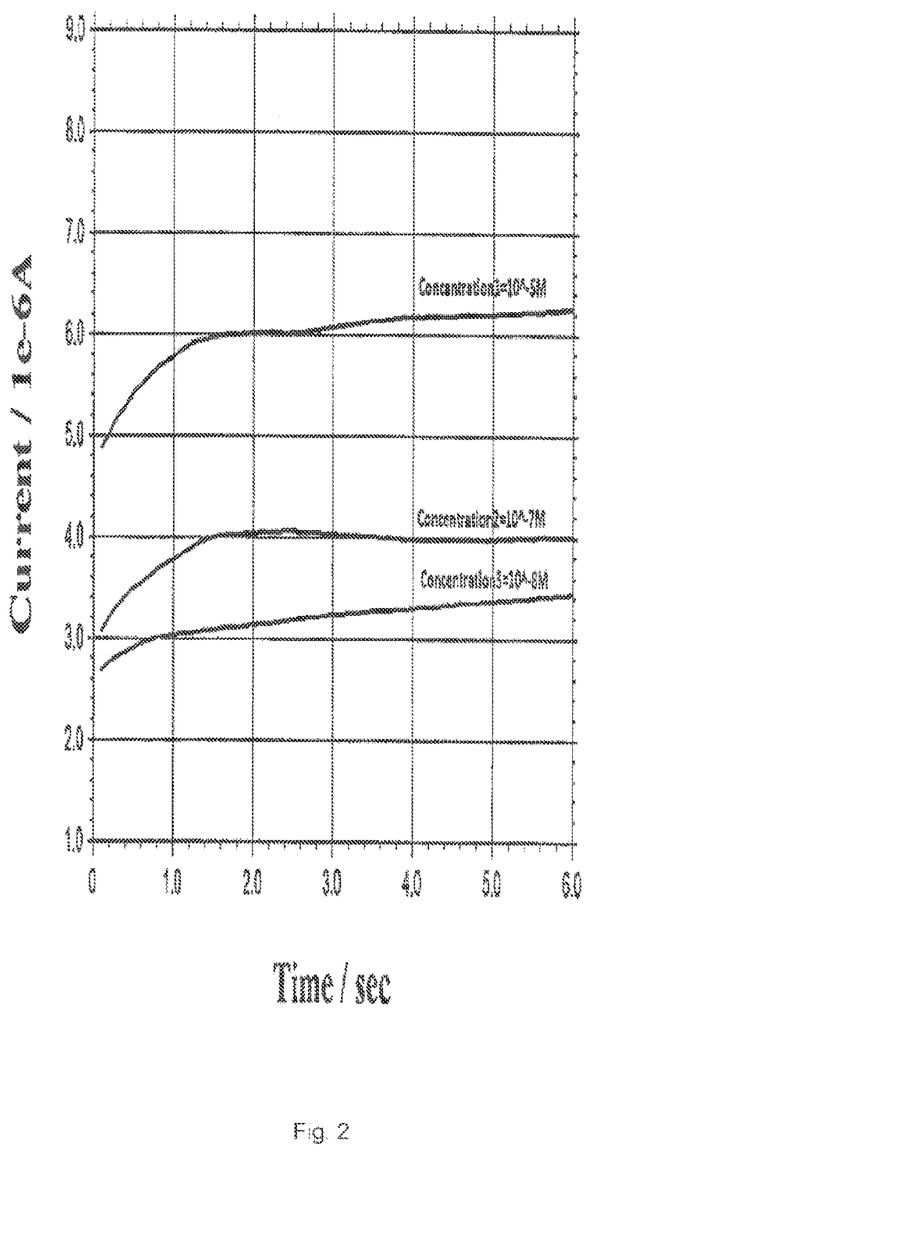
FIG. 2 illustrates a plot showing amperometric measurement of lead ion concentration in tap water over the lead ion concentration of $10^{-8}$ to $10^{-5}$ M.

As an example to demonstrate this under-potential deposited bismuth gold film based electrochemical sensor which can detect lead ions in water test medium, lead (II) nitrate is used providing the lead ions in the test medium. Tap water from Cleveland water District is used as the test medium. FIG. 2 shows the testing results demonstrating the performance this lead ion detection sensor.

During operation, a sample comprising lead ions can be applied to the working electrode for a defined length of time effective to provide deposition of the lead ions on the bismuth monolayer. The lead ions in the sample complex forming Pb(Bi) on the bismuth monolayer. Differential pulse voltammetry (DPV) measurement of the anodic stripping current of the lead ions can then be used to quantify the lead ions in the sample. The stripping reaction of lead from the bismuth layer is an irreversible reaction. Faradic current, a diffusional control reaction influenced by concentration difference, is measured by DPV. The measured current can then be compared to a control value or calibration curve to determine the concentration of lead in the sample.

By way of example, amperometric measurement of the lead ions in a sample, such as a drinking water sample, using this under-potential deposited bismuth monolayer gold film based electrochemical sensor is shown in FIG. 2. The measurement can be uses a CHI 660 Model C Electrochemical Workstation. Any other electrochemical analytical system can be used in this measurement. In a typical example, a 90 seconds incubation time is used after 15 µL of the testing solution containing the lead ions is used before the amperometric measurement is made. Any other length of incubation time can be used and to optimize the detection process. This amperometric measuring result is based on the anodic stripping of the lead ions which are adhered to the under-potential deposited monolayer or thin layers of bismuth. A fixed time for the stripping process is used and the length of this stripping time can be varied as desired.

Example

In this example, we describe the development and use of a simple-to-use, cost-effective sensor system for the detection of lead ions in water. This lead ion detection sensor used a thin gold film based electrochemical sensor with a thin layer of bismuth. The bismuth layer was deposited on the gold film based electrode elements by under-potential deposition technique. Under-potential deposition provided a monolayer or sub-layer of the bismuth on the gold electrode elements enhancing the sensitivity of detecting lead ions by the bismuth film. Subsequently, the overall sensitivity of the sensor increased. Differential pulse voltammetry (DPV) was the transduction mechanism used for this sensor system. Differential pulse voltammetry (DPV) applied a linear sweep voltammetry with a series of regular voltage pulses superimposed on the linear potential sweep. Consequently, the current is measured immediately before each potential change. Thus, the effect of the charging current is minimized, achieving a higher sensitivity. Tap water from the Cleveland, Ohio, USA regional water district was used as the test medium. Lead ion concentrations of $5 \times 10^{-4}$ M to $8 \times 10^{-7}$ M in tap water were tested. Potential interference studies by other metal ions including iron III, copper II, nickel II, and magnesium II at the concentration level of $5 \times 10^{-4}$ M were carried out, demonstrating that the sensor processed excellent selectivity without interference by any of these metallic ions. Characterization of the bismuth was performed using Time-of-Flight Secondary Ion Mass Spectrometry (TOF-SIMS) and X-ray Photoelectron Spectroscopy (XPS). This example showed that the total detection time for lead ions in the water was within 3 min at a lead ion concentration level of $10^{-4}$ M or above, and by spending 6 min for lower lead ions concentration at $10^{-7}$ M. This operation time could be further optimized. Furthermore, the cost of fabricating and developing this single-use sensor for lead detection was estimated to be less than 2 US dollars. Thus, a simple-to-use, cost effective practical sensor for lead ion detection in water became a true reality.

Materials and Methods

Apparatus and Reagents

Bismuth(III) nitrate pentahydrate (Cat. #383074) and lead(II) nitrate (Cat. #228621) were obtained from Sigma-Aldrich (St. Louis, Mo., USA). Iron(III) sulfate pentahydrate (Cat. #AC345231000), nickel(II) sulfate hexahydrate (Cat. #N73-100), copper(II) sulfate pentahydrate (Cat. #BP346), magnesium(II) sulfate heptahydrate (Cat. #M63), sodium chloride (Cat. #S271), potassium hydroxide pellets (Cat. #P1767), concentrated H2SO4 95.0 to 98.0 w/w % (Cat. #A300) and concentrated $HNO_3$ 70% w/w % (Cat. #A200) were received from Fisher Scientific (Pittsburgh, Pa., USA). A CHI 660C (CH Instrument, Inc., Austin, Tex., USA) Electrochemical Workstation was used for DPV and electrochemical impedance spectroscopy (EIS) investigations. Similar Model CHI 660 A-E Electrochemical Workstations could also be used. All the experiments were conducted at room temperature. Characterization of the bismuth film was performed using a PHI TRIFT V nanoTOF Time-of-Flight Secondary Ion Mass Spectrometer (TOF-SIMS) and a PHI Versaprobe 5000 Scanning X-ray Photoelectron Spectrometer (XPS).

Design and Fabrication of the Sensor

This basic sensor involved a platform designed in our laboratory. It consisted of a three-electrode electrochemical configuration sensor system. Both working and counter electrodes were thin gold film of 50 nm in thickness. The thin gold film was deposited by sputtering technique on a roll-to-roll manufacturing basis. The reference electrode was a thick-film printed Ag/AgCl electrode. Laser ablation technique was used to define the size and structure of the electrode elements and the overall sensor structure. This manufacturing process employed known micro-fabrication procedures, such as sputtering physical vapor deposition, laser ablation, and thick film printing techniques, resulting in a high-reproducible and low-cost single-use disposable sensor which was very beneficial for simple-to-use, disposable, cost effective in situ applications. The overall dimensions of an individual lead ion detection sensor were 33.0×8.0 $mm^2$. The working electrode area was 1.54 $mm^2$ accommodating 10-25 µL of liquid test sample. Details of the design and fabrication of this platform thin gold-film based sensor were given elsewhere.

Modification and Preparation of the Lead Ions Sensor

Chemical Pretreatment of the Thin Gold Film Electrode Elements

A three-step chemical pretreatment procedure was applied to the sensor in order to eliminate the oxidized compounds and any other residue from the gold film electrode element surface. The purpose of pretreatment was to minimize the electrode charge transfer resistance, thereby improving the sensitivity and the reproducibility of the sensor. This pretreatment procedure was based on other reported investigation as well as in our own previous studies. Typically, a batch of eight thin gold film based sensors were immersed in a 2 M KOH solution for 15 min After rinsing with copious amounts of DI water for about 30 s, the sensors were placed in a 0.05 M $H_2SO_4$ solution (95.0 to 98.0 w/w %) for another 15 min. DI water was then used to rinse the sensor prototypes for another 30 s. The sensors were then placed in a 0.05 M $HNO_3$ solution (70% w/w %) for another 15 min. The sensors were rinsed one more time with DI water for 30 s and dried gently in a steam of nitrogen. The EIS study of this pretreated sensor showed excellent reproducibility as reported in our other studies.

Under-Potential Deposition of Bismuth on the Thin Gold Film Based Sensor

Bismuth was considered unique for lead ion detection. Thus, bismuth-modified electrochemical based electrodes were proposed for lead ion detection in different test media. One advantage of using bismuth film for the detection of lead ions was that the dissolved oxygen in the test medium did not interfere with the measurement of lead ion. Thus, the use of bismuth to detect lead ions would not require removing the dissolved oxygen in the test medium which was very attractive for practical applications. Thus, bismuth film was adopted to be used in this lead ion detection approach.

Under-potential deposition was a known electrochemical process. In this deposition process, the monolayer or sublayer of the selected metallic deposition was known to be extremely sensitive to the surface structure of the electrode, enhancing the sensitivity of electrode per se.

Figure 3:
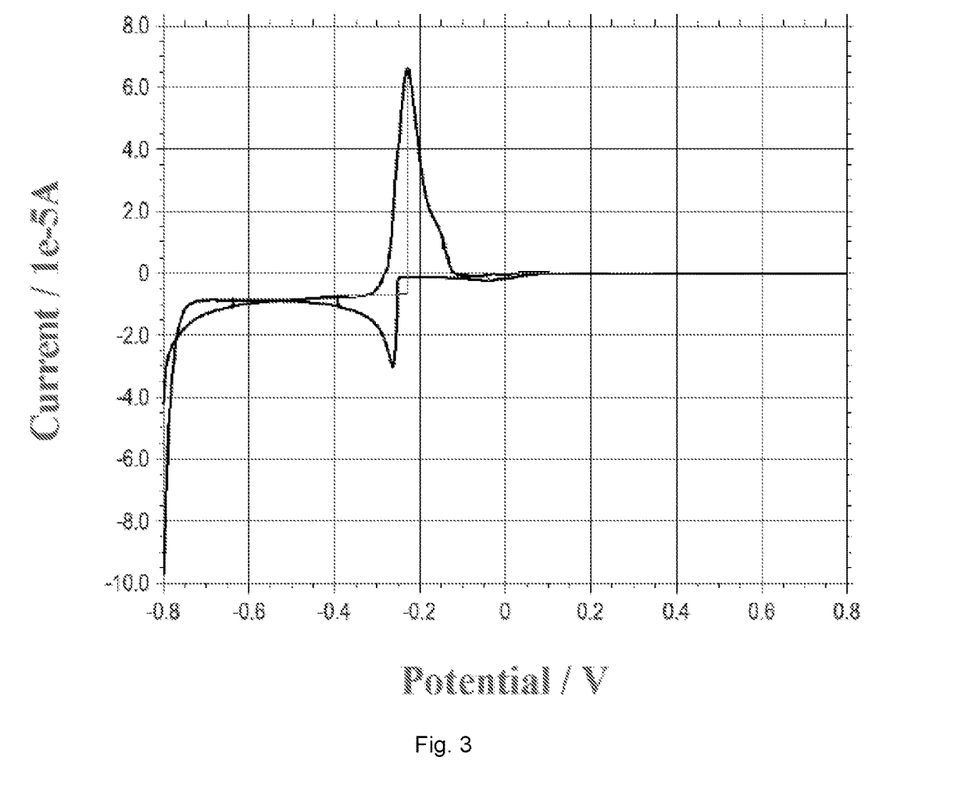
FIG. 3 illustrates a plot showing cyclic voltammetry for the full range of scanning for bismuth reaction potential.

A unique aspect of this example was that an under-potential deposited bismuth film on the thin gold film based sensor was first prepared for the lead ion detection sensor, providing the sensitivity for this lead ion detection. The under-potential deposition of bismuth might be monolayer or sub-layer. Assessment of the actual monolayer or sub-layer of bismuth film is beyond the scope of this research and will not be discussed in this study. For practical application, the under-potential deposited bismuth sub-layer provided the sensitivity of the lead ion detection sensor was our motivation in this study. In a typical preparation of this step, cyclic voltammetry was first applied for the bismuth film deposition. A bismuth ion solution was prepared. 0.025 M of Bismuth(III) nitrate pentahydrate was mixed in 1 M of nitric acid with 1 mM of sodium chloride solution. A full range of CV scan for bismuth deposition was then conducted, assessing the reduction potential for bismuth onto the gold electrode. Cathodic potentials were observed with different thicknesses of bismuth layer on the surface. For our CV study, the reduction potential of bismuth was set at −0.25 V versus the thick-film printed Ag/AgCl reference electrode as shown in FIG. 3. In a typical experience, 20 µL of prepared bismuth solution was placed on the sensor and a potential sweep from −0.50 V to −0.40 V of the cyclic voltammetry was used for the under-potential deposition of the bismuth on the gold electrode. After deposition, the bismuth sensor was rinsed with deionized water for 10 s and dried gently by nitrogen. This preparation step of this under-potential deposition of bismuth film could be accomplished prior to the actual water sample testing. FIG. 3 shows the typical CV used for this under-potential deposited bismuth film. Bismuth layer was visible and prepared sensors could then be stored at 4° C., ready for use.

Surface Characterization of Bismuth Sublayer with XPS and Tof-SIMS

The bismuth sub-layer formed by the under-potential deposition described above was examined using X-ray Photoelectron Spectroscopy and Time-of-Flight Secondary Ion Mass Spectrometry (TOF-SIMS). In this characterization study, two different bismuth concentrations were used, sample A (0.1 M) and sample B (0.25 M) of bismuth nitric solutions.

Figure 4:
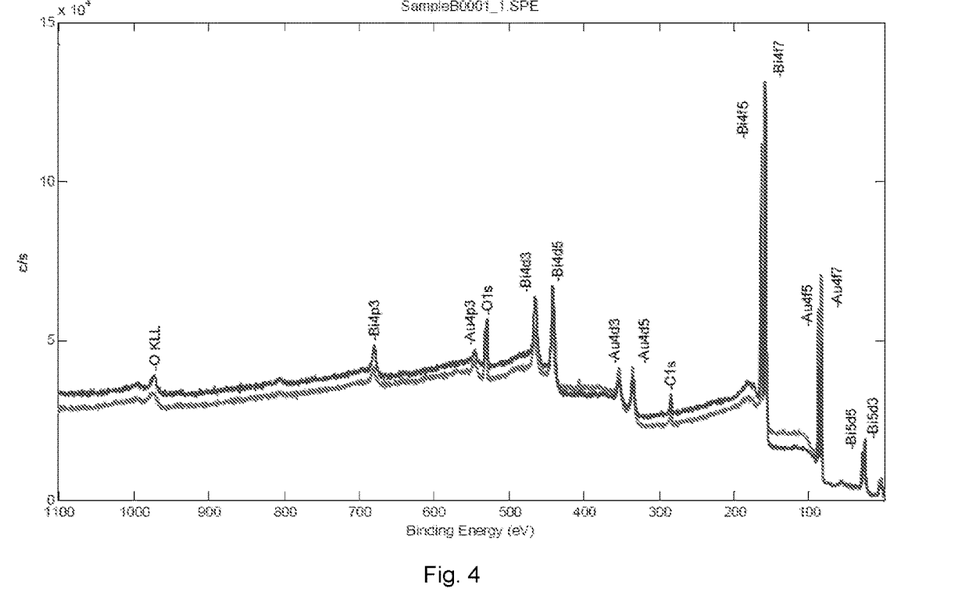
FIG. 4 illustrates plots showing a survey scan from XPS measurements at 90 degrees take of angle comparing samples A and B.
Figure 5:
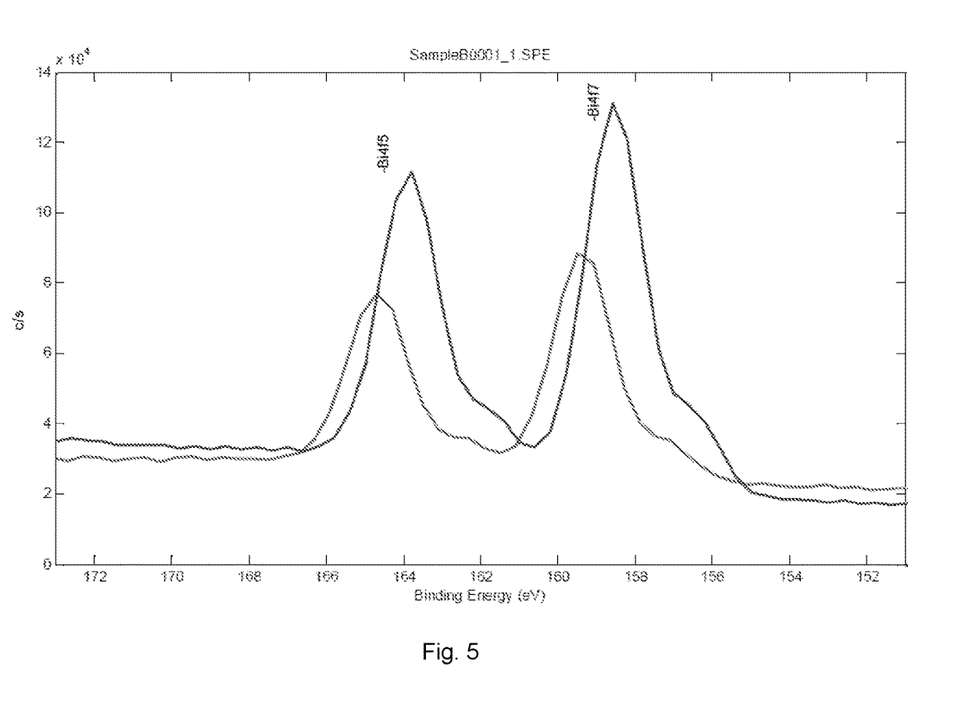
FIG. 5 illustrates plots showing bismuth 4d 7/2 peak from the Survey spectrum compared for samples A and B.

FIGS. 4 and 5 and Table 1 show the XPS analysis of the bismuth film deposited, quantifying the bismuth film composition acquired with a monochromated aluminum K alpha X-ray with an energy of 1486.7 eV and a spot size of 200 µm. The spectrum was acquired with a 90 degree take off angle to increase the surface sensitivity. The survey scan was acquired with a Band pass of 93.9 eV. An average of eight rounds of acquisition on a range of 0 to 1100 eV was scanned every 0.4 eV for 25 ms.

FIGS. 4 and 5 show the bismuth sublayer was successfully deposited by the under-potential deposition technique. As expected and demonstrated in FIG. 5, the 0.25 M of bismuth nitric solution provided a better coverage of the gold film based sensor. Therefore, 0.25 M of bismuth nitric solution was used throughout this investigation. Table 1 shows the XPS results of the atomic percentage of the samples A and B with the higher bismuth atomic percentage in sample B.

TABLE 1

| Concentration of different elements (in Atomic Percent) compared for samples A and B | | | | |
|---|---|---|---|---|
| Sample No. | C1s | O1s | Au4f | Bi4f |
| Sample A | 31.1 | 40.7 | 15.2 | 13.0 |
| Sample B | 27.5 | 40.5 | 10.3 | 21.8 |

ToF-SIMS measurements were performed in the negative polarity. At this negative polarity, bismuth and gold provided good information with a primary source of Ga. Experimentally, the primary source was a Ga+ beam accelerated to 30 KV and bunched to a pulse size of 7 ns and an acquisition rate of 22 KHz. Using this setting, the surface of the electrode could be mapped with a spatial resolution of 500 nm. Map stitching was then used to generate ion maps with a total area of 2×2 mm.

Figure 6:
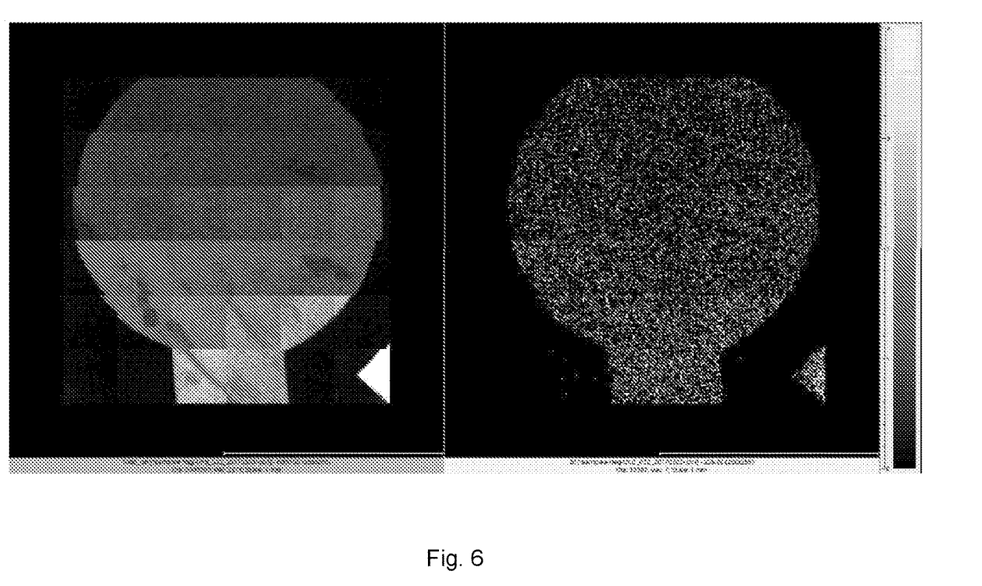
FIG. 6 illustrates images showing the total secondary ions acquired at the negative polarity of gold (left) and the bismuth ion image (right) using a Ga+ primary source.

FIG. 6 shows the TOF-SIMS analysis of the under-potential deposited bismuth structure on the gold film based sensor. FIG. 6 (left) shows the gold film based working electrode element of sensor, and FIG. 6 (right) shows the bismuth film deposited on the gold based working electrode element using a 0.25 M bismuth nitric solution and at an electrochemical potential range of −0.45 V to −0.35 V vs. an Ag/AgCl thick film printed reference electrode.

The homogeneity of the bismuth film was evident. The compositions of the bismuth film deposited was mainly bismuth, as expected. Also as expected, the bismuth film deposited with the concentration of 0.25 M bismuth nitric solution was higher than that with 0.1 M bismuth nitric solution (data did not included).

Results and Discussion

Anodic Stripping of Lead Ions by Differential Pulse Voltammetry (DPV)

Figure 7:
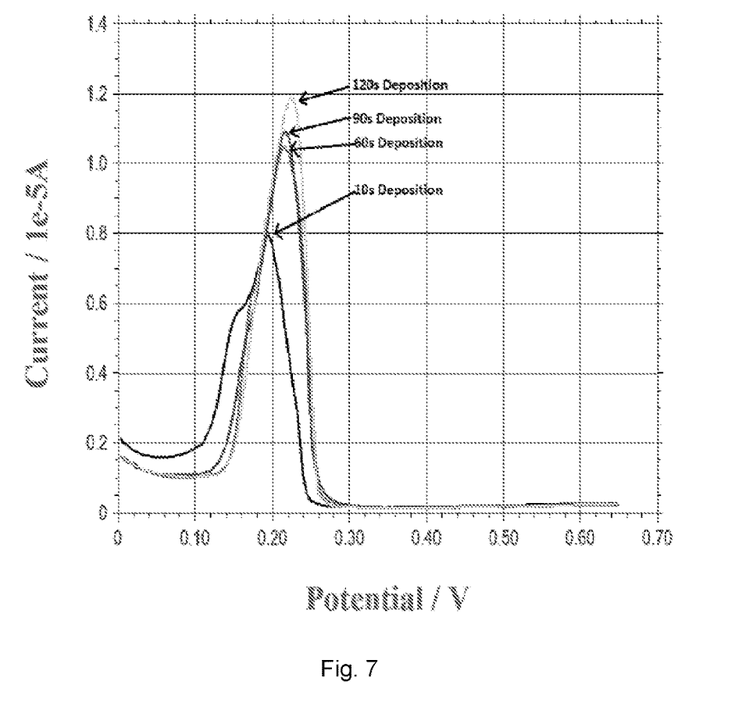
FIG. 7 illustrates plots showing electrochemical stripping analysis of lead ions for different deposition time ranging from 10 s to 120 s.

Lead ions deposited on the bismuth sub-layer was a time-dependent. The lead ions in the test medium reduced forming Pb(Bi) complex on the bismuth sub-layer. The DPV measurement of the anodic stripping current of the lead ions was then used to quantify the lead ions in the test medium. As expected, the longer the time that allowed the lead ions to be attached to the bismuth sub-layer, the higher the resulting anodic stripping current measured by DPV. In this phase of the study, tap water with $8\times10^{-4}$ M lead ions was used as the test medium. The period of time (the retention time) for the lead ions deposited on the bismuth sub-layer varied between 10 to 120 s. Typically, 20 μL of the test water sample was placed on top of the sensor surface. After the retention time, DPV measurement was then carried out. As expected, the highest anodic stripping current was obtained at 120 s, and the anodic stripping current was decreased in sequential order of 90, 60, and 10 s. Thus, 120 retention time was used in our detection of lead ions in tap water at this lead ion concentration level. The DPV measurement was completed in 60 s. Therefore, the overall time required for the detection of this lead ion level was within 3 min. This operating time has not been optimized and could be further modified. FIG. 7 shows the results of this study.

Consequently, a fixed retention, 120 s in this case, would be used for the practical application of the lead ion detection sensor system.

Detection of Lead Ions in Tap Water

Figure 8A:
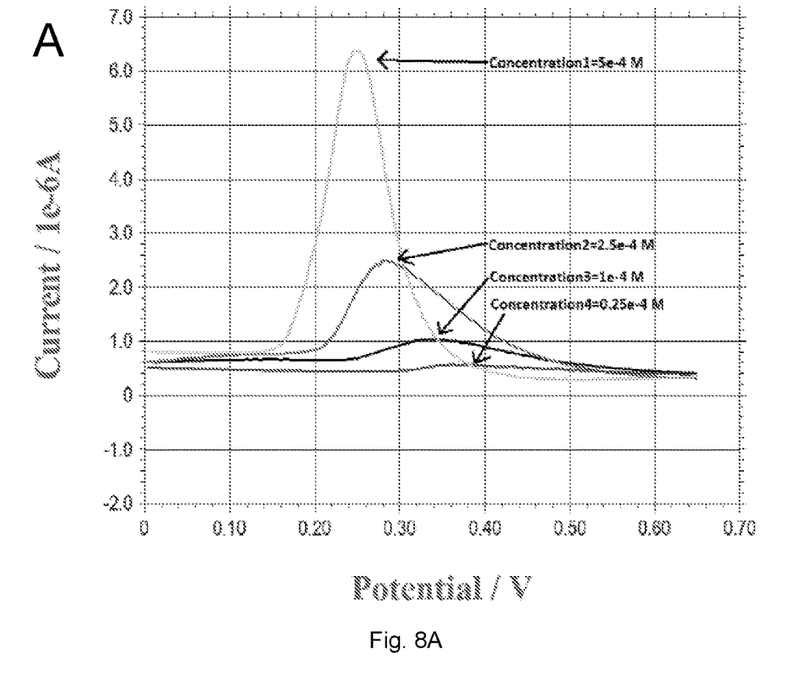
FIGS. 8A-B illustrate plots showing (A) DPV measurement of lead ions concentration level ranging from $5 \times 10^{-4}$ M to $2.5 \times 10^{-5}$ M; (B) Calibration curve for the DPV measurement data points.
Figure 8B:
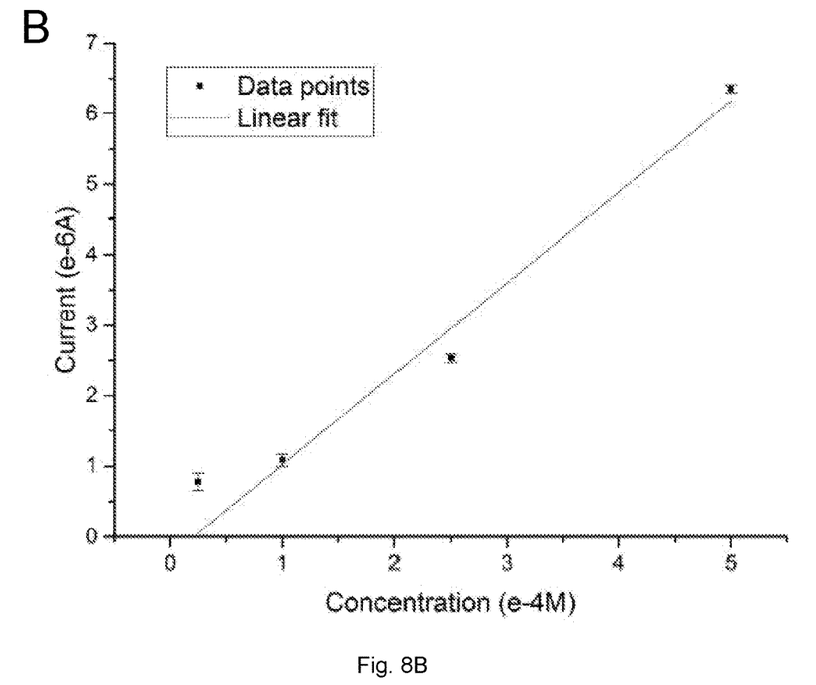

Normal tap water from the Cleveland regional water district, Cleveland, Ohio USA, was used as the test medium for this lead ion sensor detection. Lead(II) nitrate in proper quantity was added into the tap water preparing for the lead ions contained tap water test sample. In a typical experiment, 20 μL of the test water sample was placed on top of an under-potential deposited bismuth sub-layer thin gold film based sensor. At this 10−4 M lead ions concentration, a retention time period of 120 s was used based on the results. After this retention time, DPV measurement of the anodic stripping current was then undertaken. FIG. 8A shows the DPV measurement of four lead ions concentrations in the tap water, namely, $5\times10^{-4}$ M, $2.5\times10^{-4}$ M, $1\times10^{-4}$ M, and $0.25\times10^{-4}$ M with n>3. Potential shifts were observed in our DPV measurements. The stripping reaction of lead from the bismuth layer is an irreversible reaction. Faradic current, a diffusional control reaction influenced by concentration difference, was then measured by DPV technique. Also, experimental parameters, including the electrode reaction rate constant, transfer coefficient, waveform parameters, affected DPV measurement. Consequently, the minor potential shift of the DPV waveform was due to these factors. FIG. 8B shows the calibration curve based on the DPV measurements obtained in FIG. 8A. The least square fit of this calibration curve is Y=1.16 X−0.02 with R2 value of 0.970. The results of this test demonstrated that the accuracy of detecting lead ions in tap water using this under-potential deposited bismuth sublayer thin gold film based electrochemical sensor with DPV measurement was very good. The retention time was 120 s and the DPV measurement time was 60 s. Thus, the total time for the detection of lead ions could be accomplished within 180 s (3 min).

Figure 9:
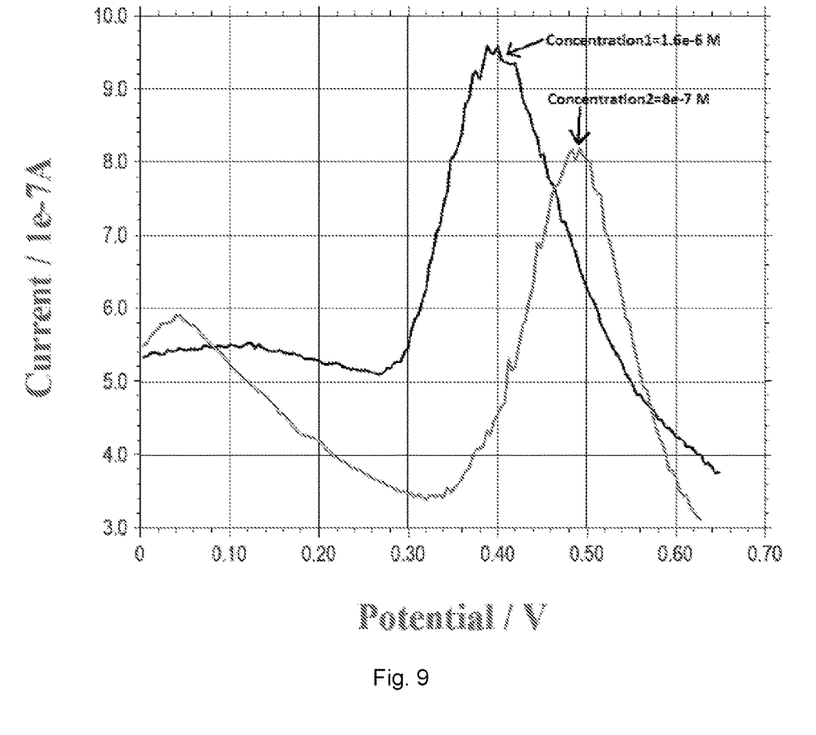
FIG. 9 illustrates a plot showing DPV measurement of lead concentration levels of $1.6 \times 10^{-6}$ M and $8 \times 10^{-7}$ M.

Lower lead ion concentrations could be detected using this under-potential deposited bismuth sub-layer on this thin gold film based sensor and with DPV measurement. The rate at which lead ions adhered to the bismuth sub-layer was a time-dependent function. Experimentally, a tap water sample containing a low level of lead ions (20 μL) was placed on top of the sensor identical to the process described above. However, at this lower lead ions concentration level, the retention time was set at 300 s (5 min), and DPV measurement was then carried out. It also required 60 s to complete the DPV measurement. FIG. 9 shows the DPV measurement of lead ions in tap water with a lead ion concentrations of $1.6\times10^{-6}$ M and $8\times10^{-7}$ M. It was apparent that this under-potential deposited bismuth sub-layer on a thin gold film sensor was capable of detecting lead ions in tap water as low as $8\times10^{-7}$ M. The detection process required a total of 360 s (6 min) using the DPV measurement technique.

Based on the results shown in FIGS. 8 and 9, a retention time of 300 s would cover the lead ions concentration range of $8\times10^{-7}$ M to $5\times10^{-4}$ M. The retention time needed for the lead ion detection can be further optimized.

Interference Study of this Lead Ions Sensor

Figure 10:
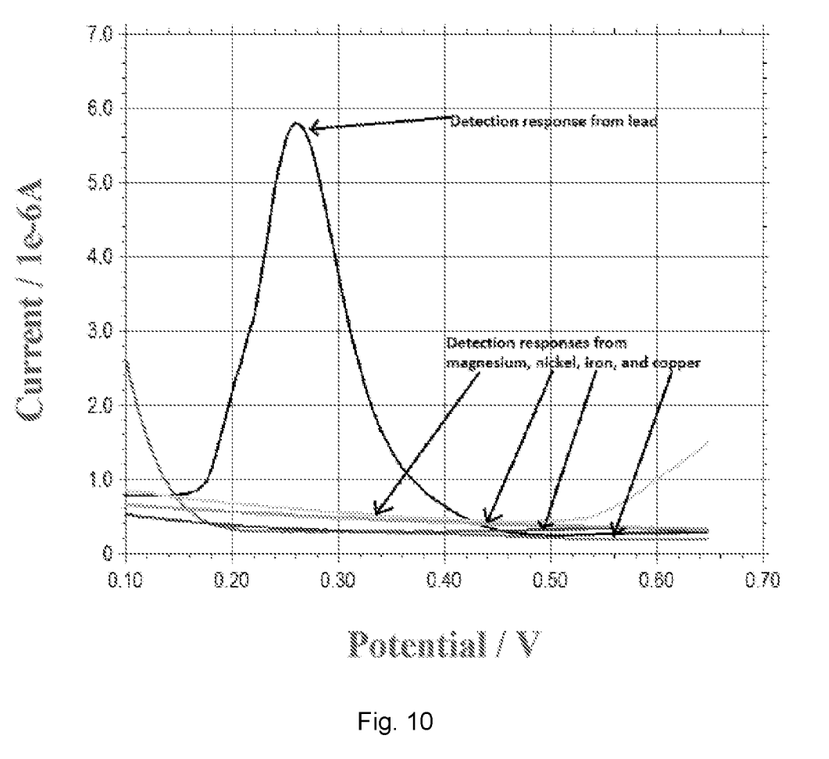
FIG. 10 illustrates a plot showing the interference test for the bismuth sensor.

Selectivity is very important for the development of a sensor. This suggested that the operation of the sensor should not interfere with other chemicals that might be presented in the test medium. Fe III, Cu II, Ni II, and Mg II and were considered to be carcinogens and may also interfere with lead bismuth reaction. Iron sulfate pentahydrate, cooper sulfate pentahydrate, nickel sulfate hexahydrate, and magnesium sulfate heptahydrate were used. Each of these chemicals was used to prepare a $5\times10^{-4}$ M concentration test sample with the Cleveland regional water district tap water. Similar to the test procedure described above, 20 μL of the water sample was placed on top of a prepared lead ion sensor. The retention time was set at 300 s ensuring that the metal ions were anodic stripped from the bismuth sub-layer. DPV measurement was undertaken after the retention time 300 s. Similar to our standard test, the DPV measurement took 60 s. FIG. 10 shows that none of the Fe III, Cu II, Ni II, and Mg II at $5\times10^{-4}$ M in tap water contribute to the DPV measured current of $5\times10^{-4}$ M lead ions in the tap water sample. This result indicated the excellent selectivity of the under-potential deposited bismuth sub-layers of a thin gold film based sensor for lead ion detection.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention the following is claimed:

1. A sensor for the detection of lead comprising:
a substrate;
a working electrode formed on a surface of the substrate;
a counter electrode formed on the surface of the substrate;

a dielectric layer covering a portion of the working electrode and counter electrode and defining an aperture exposing other portions of the working electrode and counter electrode; wherein the working electrode includes a metalized film with working surface and an atomic monolayer or bilayer of bismuth deposited on the working surface by underpotential deposition.

2. The sensor of claim 1, wherein working surface of the metalized film is substantially free of surface adsorbed impurities between the metalized film and the atomic monolayer or bilayer.

3. The sensor of claim 1, wherein the working electrode and counter electrode independently comprise gold, platinum, palladium, silver, carbon, alloys thereof, and composites thereof.

4. The sensor of claim 1, the metalized films are provided on the surface of the substrate by sputtering or coating the films on the surface and wherein the working electrode and the counter electrode are formed using laser ablation.

5. The sensor of claim 1, further comprising a reference electrode on the surface of the substrate, the dielectric covering a portion of the reference electrode.

6. The sensor of claim 1, further comprising a measuring device for applying voltage potentials to the working electrode and counter electrode and measuring the current flow between the working electrode and counter electrode.

7. A method of detecting the quantity of lead in an aqueous sample, the method comprising:
providing a sensor that includes a substrate, a working electrode formed on a surface of the substrate; a counter electrode formed on the surface of the substrate; a dielectric layer covering a portion of the working electrode and counter electrode and defining an aperture exposing other portions of the working electrode and counter electrode, wherein the working electrode includes a metalized film with working surface and an atomic monolayer or bilayer of bismuth deposited on the working surface by underpotential deposition,
applying a volume of an aqueous sample on the working electrode for a duration of time effective to allow lead ions in the sample to complex with the deposited bismuth;
anodic stripping the complexed lead ions;
measuring an anodic stripping current during anodic stripping; and
comparing the measured anodic stripping current to a control value to detect the quantity of lead ions in the aqueous sample.

8. The method of claim 7, wherein the complexed lead ions are anodically stripped by differential pulse voltammetry.

9. The method of claim 7, wherein the control value is a calibration curve.

10. The method of claim 7, wherein working surface of the metalized film is substantially free of surface adsorbed impurities between the metalized film and the atomic monolayer or bilayer.

11. The method of claim 7, wherein the working electrode and counter electrode independently comprise gold, platinum, palladium, silver, carbon, alloys thereof, and composites thereof.

12. The method of claim 7, the metalized films are provided on the surface of the substrate by sputtering or coating the films on the surface and wherein the working electrode and the counter electrode are formed using laser ablation.

13. The method of claim 7, further comprising a reference electrode on the surface of the substrate, the dielectric covering a portion of the reference electrode.

14. The method of claim 7, further comprising providing a measuring device for applying voltage potentials to the working electrode and counter electrode, and for measuring the current flow between the working electrode and counter electrode.

* * * * *